United States Patent
Liu et al.

(10) Patent No.: US 9,982,011 B2
(45) Date of Patent: May 29, 2018

(54) LEGUMAIN ACTIVATED DOXORUBICIN DERIVATIVE AS WELL AS PREPARATION METHOD AND APPLICATION THEREOF

(71) Applicant: Yafei (Shanghai) Biopharmaceutical Co., Ltd., Shanghai (CN)

(72) Inventors: Cheng Liu, Shanghai (CN); Yuan Liu, Shanghai (CN)

(73) Assignee: Yafei (Shanghai) Biopharmaceutical Co., Ltd., Shanghai (CN)

( * ) Notice: Subject to any disclaimer, the term of this patent is extended or adjusted under 35 U.S.C. 154(b) by 87 days.

(21) Appl. No.: 14/655,869

(22) PCT Filed: Dec. 23, 2013

(86) PCT No.: PCT/CN2013/001620
§ 371 (c)(1),
(2) Date: Dec. 21, 2016

(65) Prior Publication Data
US 2017/0106094 A1   Apr. 20, 2017

(30) Foreign Application Priority Data
Dec. 26, 2012   (CN) .......................... 2012 1 0573744

(51) Int. Cl.
*C07K 1/107* (2006.01)
*C07K 5/103* (2006.01)
(Continued)

(52) U.S. Cl.
CPC .......... *C07K 1/1077* (2013.01); *A61K 31/704* (2013.01); *A61K 47/542* (2017.08);
(Continued)

(58) Field of Classification Search
None
See application file for complete search history.

(56) References Cited

U.S. PATENT DOCUMENTS

2009/0175873 A1* 7/2009 Liu ...................... A61K 31/337
424/139.1

* cited by examiner

*Primary Examiner* — Jeanette M Lieb
(74) *Attorney, Agent, or Firm* — Lewis Kohn & Walker LLP; David M. Kohn; Kari Moyer-Henry

(57) ABSTRACT

The present invention discloses doxorubicin derivatives for targeted activation by Legumain, its preparation method and use. The doxorubicin derivatives are obtained by condensation between the amino group of compound A and the carboxyl group of compound B and have the following structure:

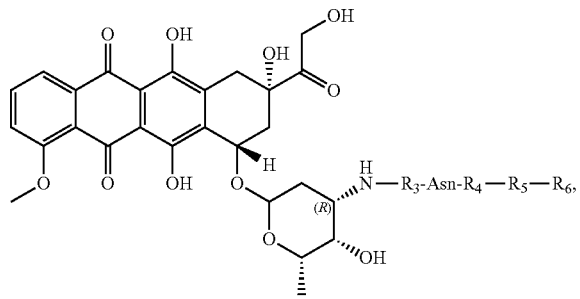

compounds A and B have the following structures, respectively:

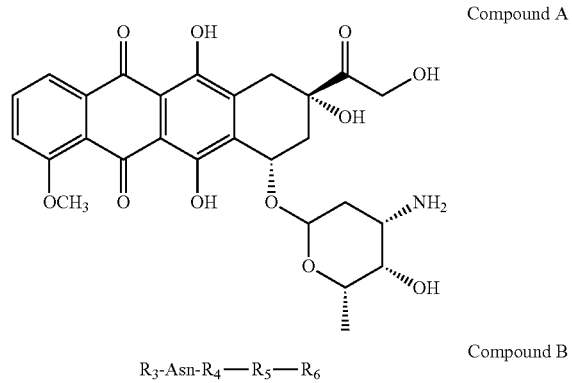

wherein $R_3$ in compound B is Len or absent; $R_4$ is any one amino acid selected from the group consisting of Ala and Thr; $R_5$ is any one amino acid selected from the group consisting of Ala, Thr and Asn; $R_6$ is

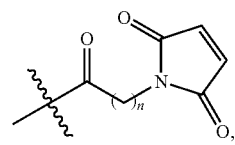

wherein n=1-20; or

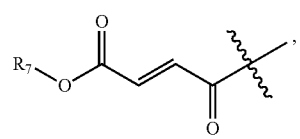

wherein $R_7$ is substituted or unsubstituted, linear or branched, saturated or unsaturated C1-C20 fatty hydrocarbon, or substituted or unsubstituted C6-C20 aromatic hydrocarbon. The doxorubicin derivatives of the present invention are specifically tumor-targeted and have a long in vivo metabolic half-life, as compared with doxorubicin. They (Continued)

exhibit an efficient and safe anti-tumor effect and could be used to prepare an anti-tumor drug.

14 Claims, 4 Drawing Sheets

(51) Int. Cl.
*C07K 19/00* (2006.01)
*C07H 15/26* (2006.01)
*C07H 15/252* (2006.01)
*A61K 31/704* (2006.01)
*A61K 47/65* (2017.01)
*A61K 47/54* (2017.01)

(52) U.S. Cl.
CPC ............ *A61K 47/545* (2017.08); *A61K 47/65* (2017.08); *C07H 15/252* (2013.01); *C07H 15/26* (2013.01); *C07K 5/101* (2013.01); *C07K 19/00* (2013.01)

LEGUMAIN ACTIVATED DOXORUBICIN DERIVATIVE AS WELL AS PREPARATION METHOD AND APPLICATION THEREOF

RELATED APPLICATIONS

This application is a United States National Stage Application claiming priority under 35 U.S.C. 371 from International Patent Application No. PCT/CN13/001620 filed on Dec. 23, 2013, which claims priority from Chinese patent application No. 2012 1 0573744.3 filed on Dec. 26, 2012, the contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 8, 2017, is named 863_201US_SL.txt and is 1,944 bytes in size.

TECHNICAL FIELD

The present invention relates to an anti-tumor compound. Specifically, the present invention relates to a doxorubicin derivative for targeted activation by Legumain, with a long metabolic half-life in vivo, and its preparation method and use.

TECHNICAL BACKGROUND

Doxorubicin (DOX) hydrochloride and epirubicin are commercially available anti-tumor antibiotics with a broad anti-tumor spectrum, killing many kinds of tumor cells, and the mechanism underlying is mainly the inhibition on the synthesis of nucleic acids upon the doxorubicin molecule inserting into DNA. Doxorubicin hydrochloride and epirubicin can be used to treat hematological tumors and solid tumors, such as breast cancer, ovarian cancer, sarcoma, and many other solid tumors. However, the dose of this kind of anthracycline compounds is restricted in clinical use because they bring serious toxicity or side effect. Doxorubicin hydrochloride can cause various unwanted effects, including bone marrow toxicity, gastrointestinal diseases, stomatitis, alopecia, exosmosis, acute and cumulative cardiac toxicity. A main limitation of doxorubicin hydrochloride lies in that, after each course of treatment, a great dose of doxorubicin hydrochloride leads to sharp reduction of monocytes and platelets in bone marrow and blood. A major concern is that a cumulative cardiac toxicity may induce a myocardial congestive heart failure, which is irreversible.

Doxorubicin (DOX) and epirubicin were functionally modified to produce effective doxorubicin based anti-tumor drugs having lower side effect.

Inventors of the subject application reported the structures and biological effects of Legubicin (BOC-AANL-DOX (SEQ ID NO: 2)) and LEG3 (Succinyl-AANL-DOX (SEQ ID NO: 2)) in Cancer Research in 2003 and 2006. However, further investigation on the drugs showed that each of both compounds is only provided with a single-targeting ability. And they had a short metabolic half-life, which leads to insufficient concentration and duration necessary for drug activation at the tumor site, and in turn, low efficacy in an animal model. Thus, they are not ideal anti-tumor drugs.

Therefore, targeting doxorubicin- and/or epirubicin-based drugs with reduced toxicity of doxorubicin hydrochloride and epirubicin and high efficacy as anti-tumor agents are in special need.

DISCLOSURE OF THE INVENTION

The present invention intends to provide a targeting doxorubicin derivative for targeted activation by Legumain, which exhibits a long metabolic half-life in vivo. The derivative only targets to and is only activated at the tumor site. Thus, it has greatly reduced toxicity and greatly increased efficacy.

To achieve the purpose, the present invention provides a doxorubicin derivative for targeted activation by Legumain, which exhibits a long metabolic half-life in vivo and has the following structural formula:

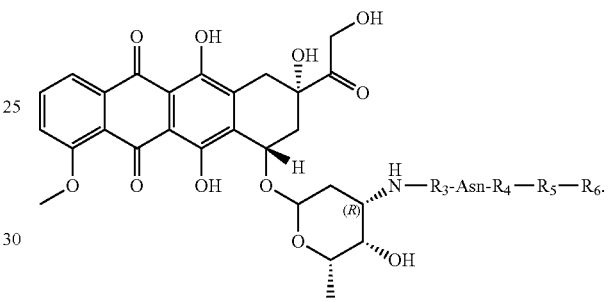

The doxorubicin derivative is prepared by condensation between amino of compound A and carboxyl of compound B, wherein compounds A and B have the following structures, respectively:

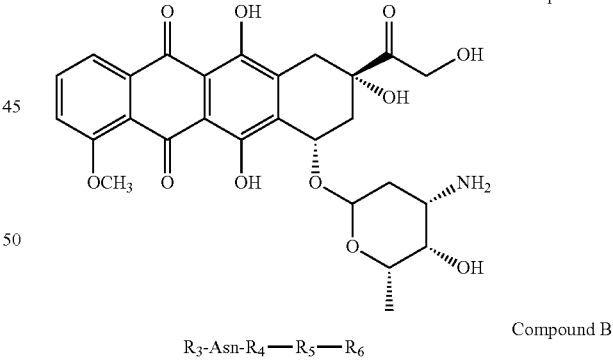

wherein $R_3$ in compound B is Leu or absent, if $R_3$ is absent then compound B is a tripeptide, that is, the carboxyl of Asn covalently condensates with the amino of compound A directly to produce apolypeptide doxorubicin; if $R_3$ is Leu, then compound B is a tetrapeptide, that is Leu-Asn-$R_4$-$R_5$—;

$R_4$ is any one amino acid selected from the group consisting of Ala and Thr;

$R_5$ is any one amino acid selected from the group consisting of Ala, Thr and Asn;

$R_6$ is

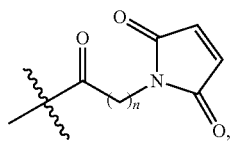

wherein n=1-20; or

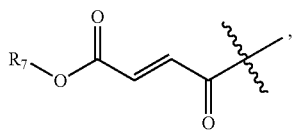

wherein $R_7$ is substituted or unsubstituted, linear or branched, saturated or unsaturated C1-C20 fatty hydrocarbon, or substituted or unsubstituted C6-C20 aromatic hydrocarbon.

Compound B ($R_3$-Asn-$R_4$-$R_6$) consists of a short peptide $R_3$-Asn-$R_4$-$R_5$— which is specifically hydrolyzed by Legumain, and a functional group $R_6$ which improves the metabolic half-life of the drug. Legumain can cleave the peptide fragment, by hydrolysis, at the position before Asn to release compound A-Asn or compound A.

In the above doxorubicin derivative for targeted activation by Legumain, compound A may be doxorubicin or epirubicin, wherein doxorubicin has the following structure:

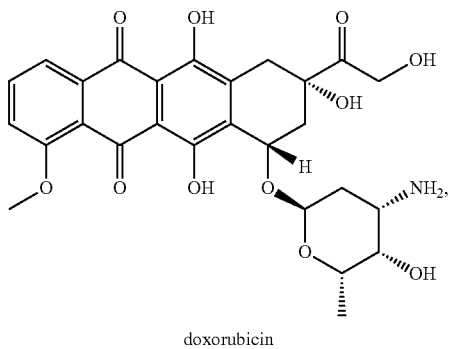 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

doxorubicin wherein epirubicin is an isomer of doxorubicin and has the following structure:

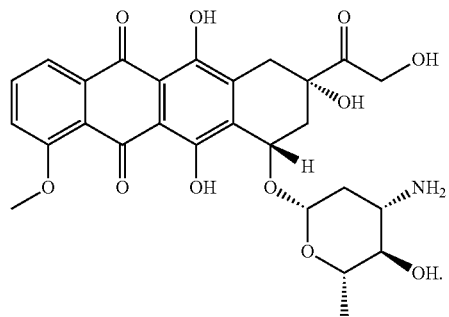 [SMILES: COc1cccc2c1C(=O)c1c(O)c3c(c(O)c1C2=O)C[C@@](O)(C(=O)CO)C[C@@H]3O[C@@H]1C[C@H](N)[C@@H](O)[C@H](C)O1]

In the above doxorubicin derivative for targeted activation by Legumain, preferably, $R_6$ is:

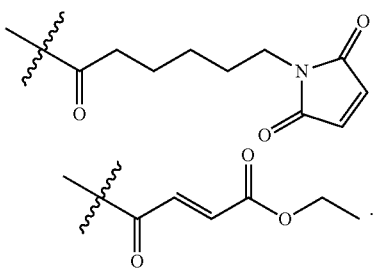

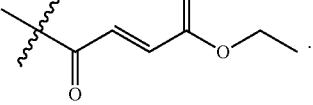

The present invention further provides a method for preparing the above doxorubicin derivative for targeted activation by Legumain, comprising the following steps:

Step 1, preparing a tripeptide or a tetrapeptide, $R_3$-Asn-$R_4$-$R_5$, by conjugating the amino acid residues together and isolating to obtain the formed tripeptide or tetrapeptide $R_3$-Asn-$R_4$-$R_5$;

Step 2, preparing compound B by reacting $R_3$-Asn-$R_4$-$R_5$ obtained in step 1 with the acyl or carboxyl of $R_6$—Cl or $R_6$—OH to obtain $R_3$-Asn-$R_4$-$R_5$-$R_6$;

Step 3, covalently combining the carboxyl in $R_3$ of the compound $R_3$-Asn-$R_4$-$R_5$-$R_6$ obtained in step 2 with the amino of compound A to form the doxorubicin derivative for targeted activation by Legumain, having a long half-life.

In the method for preparing the above doxorubicin derivative for targeted activation by Legumain, $R_3$ in compound B is Leu or absent; $R_4$ is any one amino acid selected from the group consisting of Ala and Thr; $R_5$ is any one amino acid selected from the group consisting of Ala, Thr and Asn; and $R_6$ is a drug targeting functional group, selected from group

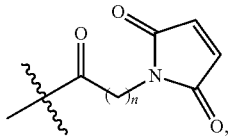

wherein n=1-20; or group

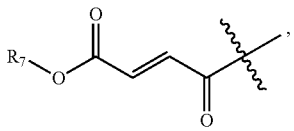

wherein $R_7$ is substituted or unsubstituted, linear or branched, saturated or unsaturated C1-C20 fatty hydrocarbon, or substituted or unsubstituted C6-C20 aromatic hydrocarbon.

In the method for preparing the above doxorubicin derivative for targeted activation by Legumain, $R_6$ is:

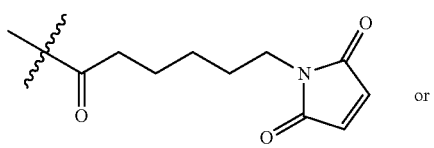

-continued

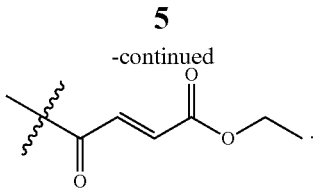

The present invention also provides use of the above doxorubicin derivative for targeted activation by Legumain in the preparation of an anti-tumor drug.

To reduce toxicity brought by an anti-tumor drug on normal cells and tissues of human body, great efforts have been made to enhance the biological specificity and selectivity of anti-tumor drugs. Recently, with development in tumor molecular biology and other basic sciences, great improvement in research and development of drugs for targeted treatment of tumors has been made. The molecular targets for the above doxorubicin derivative for targeted activation by Legumain are cathepsin (Cathepsin) and Legumain (Legumain) that generally expressed in malignant tumor cells. Both cathepsin and Legumain are proteolytic enzymes highly expressed at the tumor site. They present in most of the solid tumors and tumor microenvironment, and also distributed in a great amount in immune infiltrating macrophages and endothelial cells of the new blood vessels. Overexpression of such enzymes is highly associated with invasion of the tumor cells to the normal histiocytes, tumor metastasis and apoptosis of tumor cells.

Because of the increased permeability of blood vessels along with the growth of the tumor, high expression of the Legumain, Legumain, within the tumor microenvironment, and low pH in the local acidic microenvironment on the surface of the tumor, the modified polypeptide doxorubicin hydrochloride which is tumor microenvironment-targeting and activated, as a specific substrate of Legumain, will be effectively hydrolyzed and activated only in the tumor microenvironment, thereby releasing its cytotoxicity. Although there are also a small amount of Legumains expressed in other normal cells of a human body, this enzyme is not active in the microenvironment on the surface of normal cells. Thus, the polypeptide doxorubicin hydrochloride for targeted activation could not be hydrolyzed and activated on the surface of normal cells, and in turn causes no cytotoxicity to normal cells. Consequently, the targeted activation produces cytotoxicity only to tumor cells.

Additionally, since the drug can be completely released after the peptide chain is hydrolyzed by Legumain, we can conjugate a targeted group that can improve the efficacy of the drug to the other end of the peptide chain. After screening by experiments, the drug release and activation will not be affected and the retention of the drug at the tumor site and its anti-tumor efficiency can be improved when $R_6$ is preferably 6-maleimidocaproic (ε-maleimidocaproic, EMC) or trans-butanedioic acid monoester (EFA).

$R_6$ includes

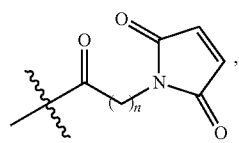

wherein n=1-20; or

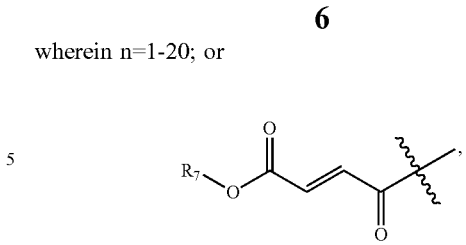

wherein $R_7$ is substituted or unsubstituted, linear or branched, saturated or unsaturated C1-C20 fatty hydrocarbon, or substituted or unsubstituted C6-C20 aromatic hydrocarbon. Preferably, $R_6$ is 6-maleimidocaproic (ε-maleimidocaproic, EMC) or trans-butanedioic acid monoester (EFA). Therefore, as compared with doxorubicin, the doxorubicin derivative for targeted activation by Legumain synthesized in the present invention exhibits both tumor-specific targeting and tumor-specific activation, and a highly efficient and safe anti-tumor effect.

In summary, the present invention provides a targeted doxorubicin derivative for targeted activation by Legumain, having a long metabolic half-life in vivo, wherein Legumain can cleave the peptide by hydrolysis at the position before Asn of the drug to release compound A-Leu or compound A. As a result, the doxorubicin of the present invention is tumor-targeted and has a long half-life. As compared with doxorubicin and epirubicin, the derivative of the present invention has a greatly improved efficacy and a greatly reduced toxicity and is thus provided with a promising application prospect.

BEST MODE FOR CARRYING OUT THE INVENTION

Figure 1:
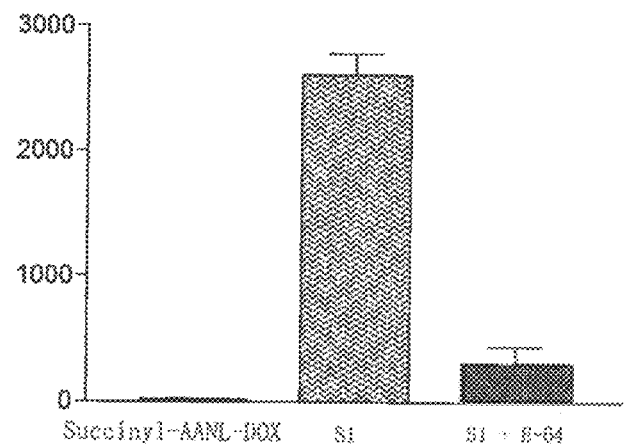
FIG. 1 is a histogram experimental result of the binding effect of S1, Succinyl-AANL-DOX (SEQ ID NO: 2) and S1+E-64 to cathepsin. The result showing that S1 can bind cathepsin and this binding can be inhibited by cathepsin inhibitor E-64.

The technical solution of the present invention is further illustrated by making reference to the Examples.

The present invention provides a method for preparing a polypeptide-doxorubicin for targeted activation by Legumain in tumor microenvironment, comprising the following steps: firstly, conjugating amino acid residues by a known chemical, biological or recombinant technique, and isolating to obtain the formed polypeptide $R_3$-Asn-$R_4$-$R_5$; secondly, reacting the N-terminal of formed polypeptide with the carboxyl or acyl of $R_6$ which can bind to albumin, by a known chemical or biological method, to form a covalent conjugate $R_3$-Asn-$R_4$-$R_5$-$R_6$; thirdly, covalently binding the carboxyl of $R_3$ in $R_3$-Asn-$R_4$-$R_5$-$R_6$ (or the carboxyl of Asn when $R_3$ is absent) to the amino of doxorubicin or salt thereof or doxorubicin derivative or salt thereof (compound A) to form a doxorubicin analogue, i.e., compound A-$R_3$-Asn-$R_4$-$R_5$-$R_6$, which has a short peptide and a targeting group. The reaction scheme is showed as follows:

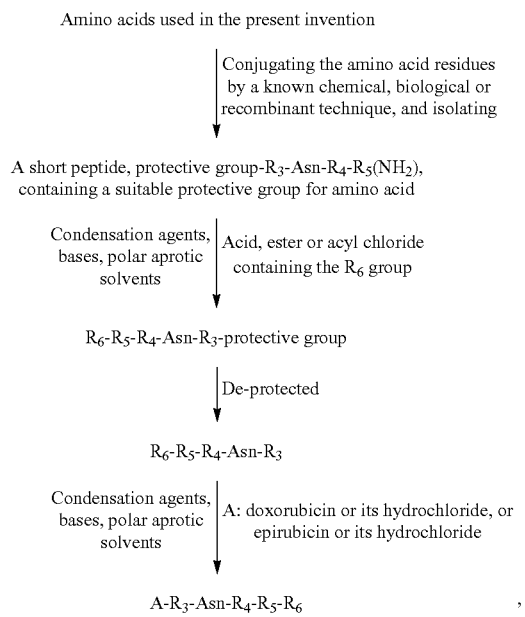

The condensation agent includes the known chemical agents used for condensation of a carboxylic acid with an amino group to form an amide, which can be used alone or in combination, such as 1-hydroxylbenzotriazol (HOBT), N,N-dicyclohexylcarbodiimide (DCC), 1-ethyl-(3-dimethylaminopropyl) carbodiimide hydrochloride (EDCI), 2-(7-azabenzotriazol-1-yl)-N,N,N',N'-tetramethyluronium tetrafluoroborate (TATU), O-(benzotriazol-1-yl)-N,N,N,N-tetramethyluronium tetrafluoroborate (TBTU), N-hydroxy-7-azabenzotriazole (HOAT), benzotriazol-1-yloxytris(dimethylamino)-phosphonium hexafluorophosphate (BOP), and benzotriazol-1-yl-oxytripyrrolidinophosphonium hexafluorophosphate (PyBOP), etc.

The base may include an inorganic base or an aprotic organic base. The inorganic base may include sodium carbonate, potassium carbonate, lithium carbonate, calcium carbonate, magnesium carbonate, sodium bicarbonate, potassium bicarbonate, calcium bicarbonate, magnesium bicarbonate, etc. The aprotic organic base may include triethylamine, N,N-diisopropylethylamine, pyridine, 4-dimethylaminopyridine, and N-methylmorpholine, etc.

Polar aprotic solvent may include N,N-dimethylformamide, dichloromethane, trichloromethane, ethyl acetate, tetrahydrofuran, acetonitrile, dioxane, methyl t-butyl ether, ethylene glycol dimethyl ether, dimethylsulfoxide, and hexamethylphosphoramide, etc.

Example 1: Synthesis of the Polypeptide Doxorubicin S1 and S2 for Targeted Activation in the Tumor Microenvironment S1 and S2 were synthesized as follows (drawing below discloses SEQ ID NO: 1 as "Ala-Ala-Asn(Trt)-Leu" and SEQ ID NO: 2 as "Ala-Ala-Asn-Leu"):

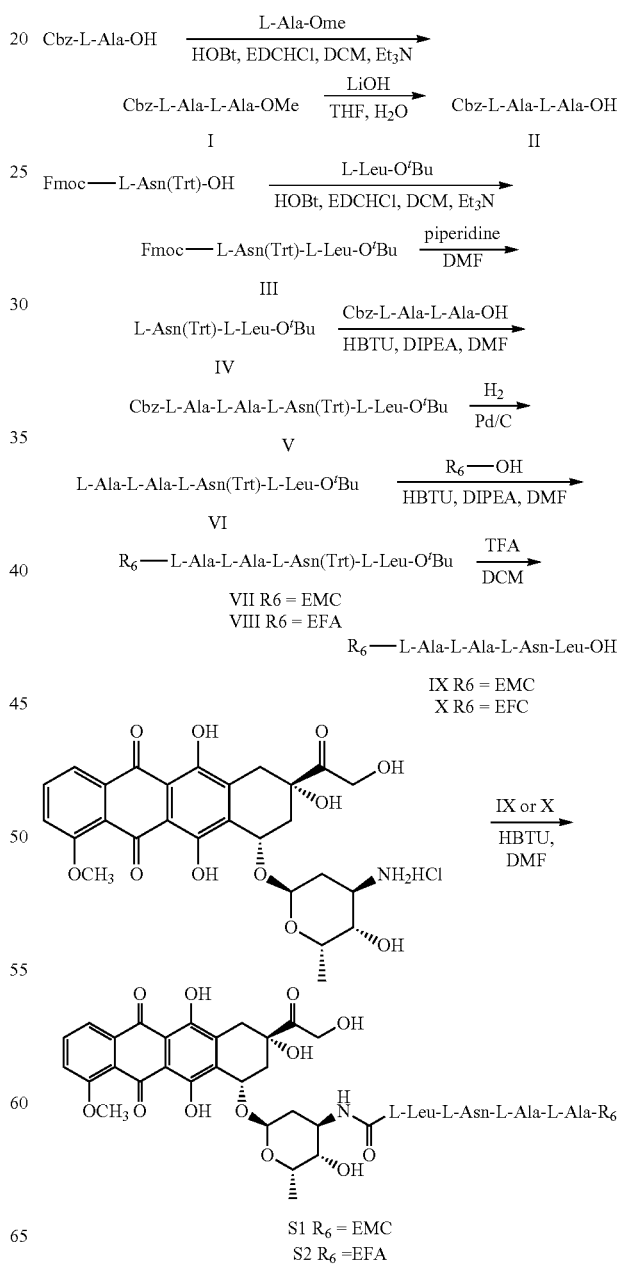

$R_6 =$ 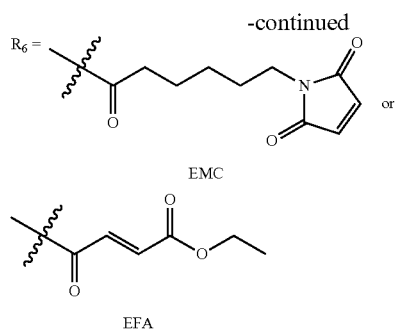 or

EMC

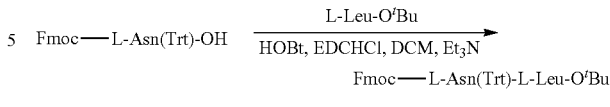

EFA

1) Synthesis of Cbz-L-Ala-L-Ala-Ome (I)

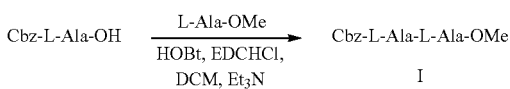

N-benzyloxycarbonyl-L-alanine (100 g, 0.45 mol) was dissolved in a dried N,N-dimethylformamide (3 L), and 1-hydroxylbenzotriazole (72.6 g, 0.54 mol) and 1-ethyl-(3-dimethylaminopropyl) carbodiimide hydrochloride (103.3 g, 0.54 mol) were added while stirring. After stirring for reaction for 1 hour, the mixture was subjected to an ice bath until the temperature reached 0° C. L-alanine methyl ester (46.2 g, 0.45 mol) and N,N-diisopropyl ethylamine (173.8 g, 1.34 mol) dissolved in an N,N-dimethylformamide (1 L) solution were dropped into the mixture. After dropping, the mixture was stirred under ambient temperature for 10 hours and the solvents were removed by evaporation under reduced pressure. The crude product was dissolved in dichloromethane (2 L) and washed successively with saturated ammonia chloride solution, water and saturated sodium chloride solution. The organic phase was dried with anhydrous sodium sulfate and the solvents were removed by evaporation under reduced pressure. The crude product was re-crystallized by ethyl acetate/petroleum ether to obtain a pure product, which was a white solid I, i.e., Cbz-L-Ala-L-Ala-OMe (101 g; Yield, 73.1%).

2) Synthesis of Cbz-L-Ala-L-Ala-OH (II)

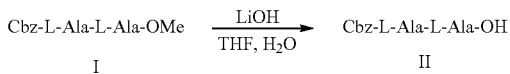

Cbz-L-Ala-L-Ala-OMe (100 g, 0.34 mol) was dissolved in a mixed solution of tetrahydrofuran (2 L) and water (1 L) and cooled to 0° C. 1 mol/L lithium hydroxide solution (400 mL) was dropped to the mixture and then stirred and reacted for 10 hours. Concentrated hydrochloric acid was dropped to the mixture to neutralize its pH to below 6. Tetrahydrofuran was removed by evaporation under reduced pressure. The residual water phase was extracted by dichloromethane (1 L×3). The organic phase was dried with anhydrous sodium sulfate and removed by evaporation under reduced pressure to obtain a white solid II, i.e., Cbz-Ala-Ala-OH (88 g; Yield, 92.2%).

3) Synthesis of Fmoc-L-Asn(Trt)-L-Leu-OtBu (III)

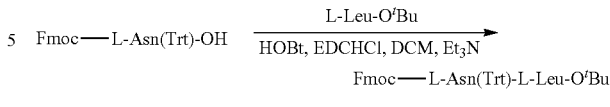

L-leucine t-butyl ester (22.4 g, 0.1 ml), N-Fmoc-N'-tribenzyl asparagine (59.6 g, 0.1 mol) were disclosed in N,N-dimethylformamide (1000 mL) in a three-necked bottle. 1-hydroxylbenzotriazol (14.85 g, 0.11 mol) and 1-ethyl-(3-dimethylaminopropyl) carbodiimide hydrochloride (23 g, 0.12 mol) were added under stirring and then the mixture was subjected to an ice bath until the temperature reached 0° C. N,N-diisopropyl ethylamine (25.8 g, 0.2 mol) was dropped and then the mixture was stirred for 10 hours. Then the solvents were removed by evaporation under reduced pressure. The crude product was dissolved in chloroform (1000 ml) and washed successively with saturated ammonia chloride solution, saturated sodium chloride solution and water. The organic phase was dried with anhydrous sodium sulfate and filtered. The solvents were removed by evaporation under reduced pressure to obtain a crude product. The crude product was purified by recrystallization (dichloromethane:ethyl acetate=1:1, by volume) to obtain a white solid III, i.e., Fmoc-L-Asn(Trt)-L-Leu-OtBu (42.4 g; Yield, 55.4%).

4) Synthesis of L-Asn(Trt)-L-Leu-OtBu (IV)

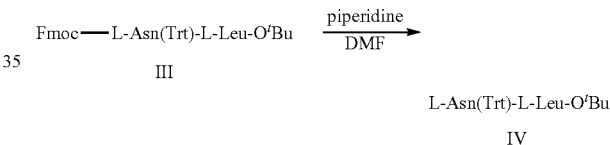

Fmoc-L-Asn(Trt)-L-Leu-OtBu (7.65 g, 0.01 mol) was dissolved in a mixed solution of dichloromethane (100 mL) and N,N-dimethylformamide (100 mL) and then piperidine (40 ml) was added. The mixture was stirring under ambient temperature for 5 hours. The solvents were removed by evaporation under reduced pressure and a small amount of residual piperidine was removed by drying under high vacuum in a high vacuum oven to produce L-Asn(Trt)-L-Leu-OtBu (IV), which was a pale yellow solid and could be used without further purification.

5) Synthesis of Cbz-L-Ala-L-Ala-L-Asn(Trt)-L-Leu-OtBu (SEQ ID NO: 1) (V) (Drawing Below Discloses SEQ ID NO: 1)

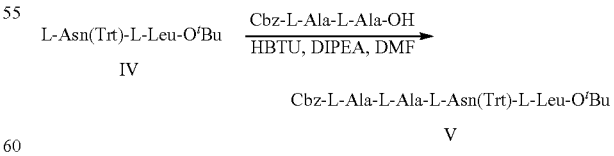

The crude L-Asn(Trt)-L-Leu-OtBu obtained in step 4) was dissolved in N,N-dimethylformamide (200 mL), and Cbz-L-Ala-L-Ala-OH (2.94 g, 0.012 mol) and benzotriazole-N,N,N',N'-tetramethyluronium hexafluophosphate (HBTU) (6.07 g, 0.016 mol) were added. The mixture was subjected to an ice bath until its temperature reached 0° C.

N,N-diisopropyl ethylamine (2.6 g, 0.02 mol) was added and then the mixture was stirred overnight under ambient temperature. The solvents were removed by evaporation under reduced pressure. The residue was dissolved in chloroform (100 ml), washed successively with saturated ammonia chloride solution and saturated sodium chloride solution, dried with anhydrous sodium sulfate, and filtered. Then the solvents were removed by evaporation. The resultant crude product was subject to silica column chromatography (dichloromethane:methanol=50:1-20:1, by volume) to produce compound V, i.e., Cbz-L-Ala-L-Ala-L-Asn(Trt)-L-Leu-OtBu (SEQ ID NO: 1), which was a white solid (3.1 g; total yield in two steps, 37.8%).

6) Synthesis of L-Ala-L-Ala-L-Asn(Trt)-Leu-OtBu (SEQ ID NO: 1) (VI) (Drawing Below Discloses SEQ ID NOS 1 and 1, Respectively, in Order of Appearance)

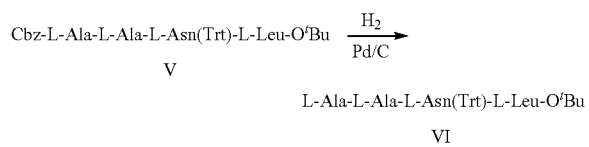

Cbz-L-Ala-L-Ala-L-Asn(Trt)-L-Leu-OtBu (SEQ ID NO: 1) (10 g, 12.2 mmol) was dissolved in methanol (400 mL) and 10% palladium-carbon (1 g) was added. After introducing hydrogen gas, the mixture was stirred for reaction under normal pressure and temperature for 4 hours. Then the reaction mixture was filtered to remove palladium-carbon and washed with methanol. The filtrate and the wash solution were pooled and the solvents contained therein were removed by evaporation under reduced pressure to obtain VI, i.e., L-Ala-L-Ala-L-Asn(Trt)-L-Leu-OtBu (SEQ ID NO: 1), which was a white solid (7.6 g; Yield, 91%).

7) Synthesis of EMC-L-Ala-L-Ala-L-Asn(Trt)-L-Leu-OtBu (SEQ ID NO: 1) (VII) (Drawing Below Discloses SEQ ID NOS 1 and 1, Respectively, in Order of Appearance)

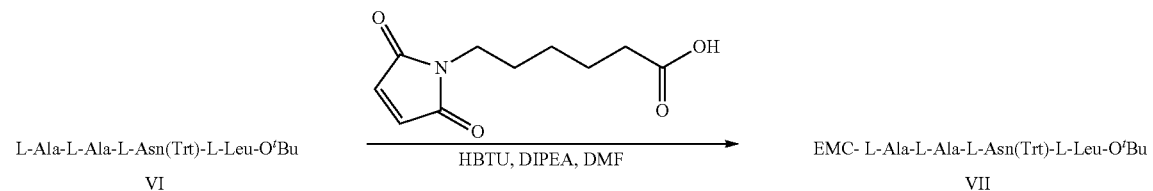 [SMILES: O=C(O)CCCCCN1C(=O)C=CC1=O ; "VI" ; "VII"]

6-Maleimidocaproic acid (1.02 g, 4.82 mmol) was dissolved in N,N-dimethylformamide (60 mL), and benzotriazole-N,N,N',N'-tetramethyluronium hexafluophosphate (HBTU) (2.49 g, 6.57 mmol) was added. Then the mixture was stirred under ambient temperature for half an hour and subjected to an ice bath until its temperature reached 0° C. L-Ala-L-Ala-L-Asn-L-Leu-OtBu (SEQ ID NO: 2) (3 g, 4.38 mmol) and N,N-diisopropyl ethylamine (1.13 g, 8.76 mmol) dissolved in N,N-dimethylformamide (60 mL) were dropped into the mixture. After dropping, the mixture was warmed up to ambient temperature and then stirred for 10 hours. The solvents were removed by evaporation under reduced pressure. The residue was dissolved in dichloromethane (200 mL) and washed successively with saturated ammonia chloride solution and saturated sodium chloride solution, dried with anhydrous sodium sulfate, and filtered. Then the solvents were removed by evaporation under reduced pressure. The resultant crude product was subjected to silica column chromatography (dichloromethane:methanol=50:1-20:1, by volume) to produce compound VII, i.e., EMC-L-Ala-L-Ala-L-Asn(Trt)-L-Leu-OtBu (SEQ ID NO: 1), which was a pale yellow solid (2.52 g; total yield in two steps, 65.46%).

8) Synthesis of EFA-L-Ala-L-Ala-L-Asn-L-Leu-OtBu (SEQ ID NO: 2) (VIII) (Drawing Below Discloses SEQ ID NOS 1 and 1, Respectively, in Order of Appearance)

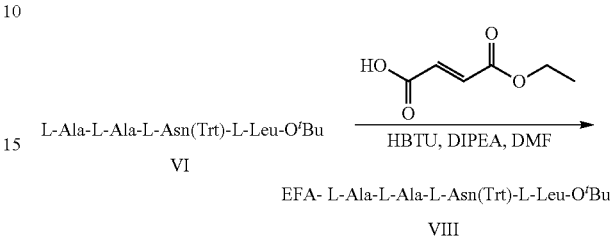

Monoethyl fumarate (0.69 g, 4.82 mmol) was dissolved in N,N-dimethylformamide (60 mL), and benzotriazole-N,N,N',N'-tetramethyluronium hexafluophosphate (HBTU) (2.49 g, 6.57 mmol) was added. Then the mixture was stirred under ambient temperature for half an hour and subjected to an ice bath until its temperature was below 0° C. L-Ala-L-Ala-L-Asn-L-Leu-OtBu (SEQ ID NO: 2) (3 g, 4.38 mmol) and N,N-diisopropyl ethylamine (1.13 g, 8.76 mmol) dissolved in N,N-dimethylformamide (60 mL) were dropped into the mixture. After dropping, the mixture was warmed up to ambient temperature and then stirred for 10 hours. The solvents were removed by evaporation under reduced pressure. The residue was dissolved in dichloromethane (200 mL) and washed successively with saturated ammonia chloride solution and saturated sodium chloride solution, dried with anhydrous sodium sulfate, and filtered. Then the solvents were removed by evaporation under reduced pressure. The resultant crude product was subjected to silica column chromatography (dichloromethane:methanol=50:1-20:1, by volume) to produce compound VIII, i.e., EFA-L-Ala-L-Ala-L-Asn(Trt)-L-Leu-OtBu (SEQ ID NO: 1), which was a pale yellow solid (2.10 g; Yield, 59.15%).

9) Synthesis of EMC-L-Ala-L-Ala-L-Asn-L-Leu-OH (SEQ ID NO: 2) (IX) (Drawing Below Discloses SEQ ID NOS 1 and 2, Respectively, in Order of Appearance)

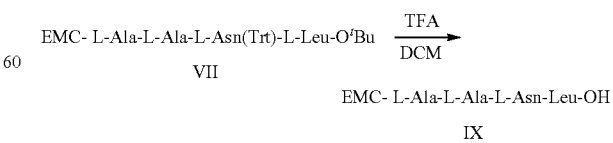

EMC-L-Ala-L-Ala-L-Asn(Trt)-L-Leu-OtBu (SEQ ID NO: 1) (1 g, 1.68 mmol) was dissolved in dichloromethane (50 mL), and trifluoroacetic acid (10 mL) was added. The mixture was stirred under ambient temperature for 10 hours. The reaction solution was washed with water and then separated. The organic phase was dried with anhydrous sodium sulfate and the solvents were removed by evaporation under reduced pressure. The residual trifluoroacetic acid was removed by evaporation under high vacuum to produce a white solid IX, i.e., EMC-L-Ala-L-Ala-L-Asn-L-Leu-OH (SEQ ID NO: 2) (0.60 g; Yield, 90.9%).

10) Synthesis of EFA-L-Ala-L-Ala-L-Asn-L-Leu-OH (SEQ ID NO: 2) (X) (Drawing Below Discloses SEQ ID NOS 1 and 2, Respectively, in Order of Appearance)

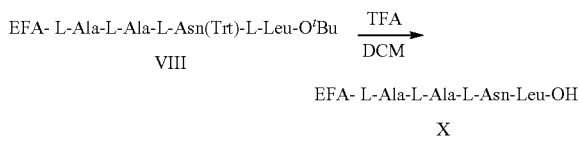

EFA-L-Ala-L-Ala-L-Asn(Trt)-L-Leu-OtBu (SEQ ID NO: 1) (1 g, 1.23 mmol) was dissolved in dichloromethane (50 mL), and trifluoroacetic acid (10 mL) was added. The mixture was stirred under ambient temperature for 10 hours. The reaction solution was washed with water and then separated. The organic phase was dried with anhydrous sodium sulfate and the solvents were removed by evaporation under reduced pressure. The residual trifluoroacetic acid was removed by evaporation under high vacuum to produce a white solid X, i.e., EFA-L-Ala-L-Ala-L-Asn-L-Leu-OH (SEQ ID NO: 2) (0.51 g; Yield, 80.9%).

11) Synthesis of EMC-AANL-Doxorubicin (SEQ ID NO: 2) (S1) (Drawing Below Discloses SEQ ID NO: 2)

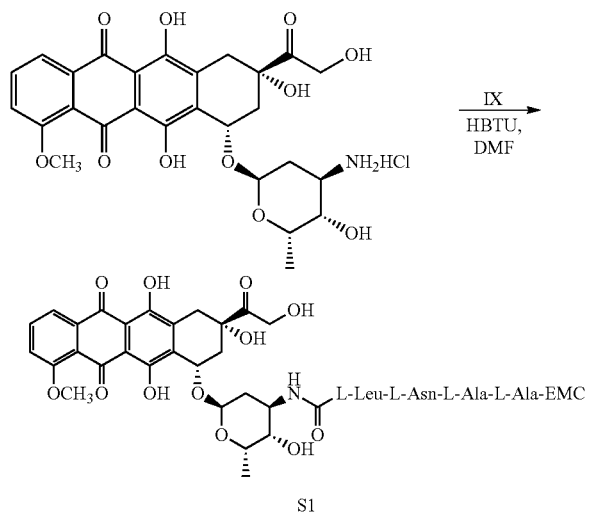

EMC-L-Ala-L-Ala-L-Asn-L-Leu-OH (SEQ ID NO: 2) (0.5 g, 0.85 mmol) and N-methyl morpholine (0.18 g, 1.78 mmol) were dissolved in anhydrous N,N-dimethylformamide (20 mL) and cooled to 0° C. or below. Benzotriazole-N,N,N',N'-tetramethyluronium hexafluophosphate (HBTU) (0.49 g, 1.28 mmol) was added. After stirring for half an hour, doxorubicin hydrochloride (0.45 g, 0.78 mmol) was added. Away from light, the reaction temperature was slowly warmed up to ambient temperature and then stirred for 5 hours. The reaction solution was added to 200 mL, 0.1% acetate aqueous solution. Dichloromethane was added for extraction. The organic phases were pooled, washed with water, and dried with anhydrous sodium sulfate. The solvents were removed by evaporation under reduced pressure to obtain a crude product, which was orange red. The crude product was purified by silica column chromatography (dichloromethane/methanol) to produce the title product S1, i.e., EMC-AANL-Doxorubicin (SEQ ID NO: 2), which was a red solid (0.45 g; Yield, 52.24%). The molecular weight was 1105.45. After analysis of S1 by HPLC-MASS, its purity at the 6.99 eluting peak was 97%, and the corresponded MASS result was 1105.45. Thus the target product was confirmed as S1.

12) Synthesis of EFA-AANL-Doxorubicin (SEQ ID NO: 2) (S2) (Drawing Below Discloses SEQ ID NO: 2)

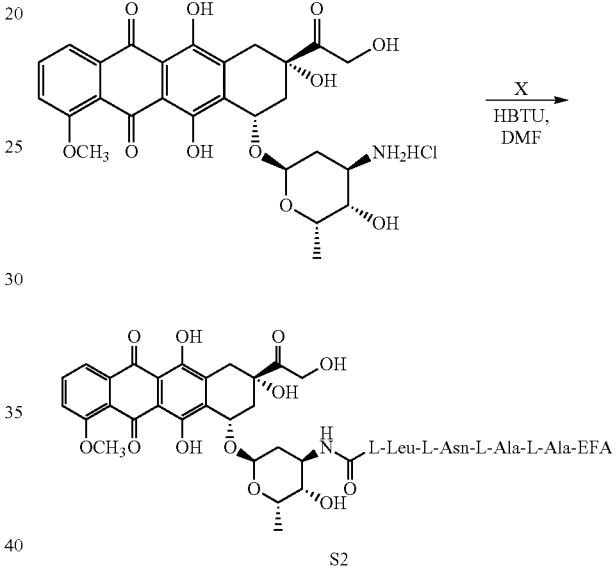

EFA-L-Ala-L-Ala-L-Asn-L-Leu-OH (SEQ ID NO: 2) (0.44 g, 0.85 mmol) and N-methyl morpholine (0.18 g, 1.78 mmol) were dissolved in anhydrous N,N-dimethylformamide (20 mL) and cooled to 0° C. or below. Benzotriazole-N,N,N',N'-tetramethyluronium hexafluophosphate (HBTU) (0.49 g, 1.28 mmol) was added. After stirring for half an hour, doxorubicin hydrochloride (0.45 g, 0.78 mmol) was added. Away from light, the reaction temperature was slowly warmed up to ambient temperature and then stirred for 5 hours. The reaction solution was added to 200 mL, 0.1% acetate aqueous solution. Dichloromethane was added for extraction. The organic phases were pooled, washed by water, and dried with anhydrous sodium sulfate. The solvents were removed by evaporation under reduced pressure to obtain a crude product, which was orange red. The crude product was purified by silica column chromatography (dichloromethane/methanol) to produce the title product S2, i.e., EFA-AANL-DOX (SEQ ID NO: 2), which was a red solid (0.40 g; Yield, 49.43%). After analysis by HPLC-MASS, the purity at the 6.99 eluting peak was 96%, and the corresponding MASS result was 11138.41. Thus the target product was confirmed as S2.

ε-Maleimidocaproic acid was synthesized according to Synthesis, 2008(8), 1316-1318 and its reaction scheme is showed below:

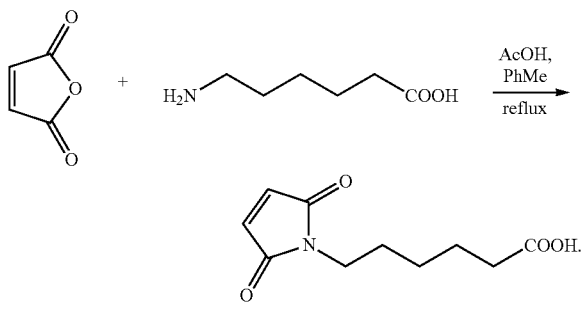

EMC

Example 2: Preparation of an Injection

The synthesized S1 and S2 were dried under vacuum to produce red powders, sterilized by gas sterilization, and separately packaged in a sterile room. Before animal experiment, the powder was dissolved in water for injection containing 50% alcohol in the sterile room and then diluted with water for injection to the desired concentration.

Example 3: Method for Determining the Contents of S1 and S2 and their Content Ranges S1 and S2 samples were analyzed by analytical type HPLC (Agilent 1100 series, equipped with C8 column of 5 μm and 4.6 mm ID×250 mm, and the mobile phase being 0-95% acetonitrile (CAN). Results showed that the purity was in the range of 95% to 99%.

The beneficial effects of the present invention were demonstrated by the following drug tolerance assays and efficacy assays.

Test Example 1: Measurement of Maximum Tolerated Dose (MTD) by Intravenous Administration of the Test Drug Test purpose: to investigate the acute toxicity of the subject new drug formulation via MTD assay by intravenous administration to mice.

Test drug: S1 and S2 injections, diluted to the corresponding concentrations with physiological saline when tested.

Animal: the first class BALB/C mice, weighing 19-21 g and all mice being female.

Method and results: 36 female BALB/C mice weighing 19-21 g were randomly divided into 6 groups according to their body weights, with 6 mice in each group. As shown in Table 1, the mice were intraperitoneally injected with S1 or S2 for just one time in a dose of 0 mg/kg, 50 mg/kg, 100 mg/kg, 150 mg/kg, 200 mg/kg or 300 mg/kg. Control tests were performed by injecting 0.2 ml physiological saline or doxorubicin hydrochloride. Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 1

Comparison of mortality rates of test mice receiving different doses of S1 and S2 injections, physiological saline or doxorubicin hydrochloride injection

| Group | | Dose (mg/kg) | Number of animal | Number of dead animal | Mortality rate (%) |
|---|---|---|---|---|---|
| 1 | physiological saline | 0 mg/kg | 6 | 0 | 0 |
| 2 | S1 | 50 mg/kg | 6 | 0 | 0 |
| 3 | S1 | 100 mg/kg | 6 | 0 | 0 |
| 4 | S1 | 150 mg/kg | 6 | 0 | 0 |
| 5 | S1 | 200 mg/kg | 6 | 2 | 33.3% |
| 6 | S1 | 300 mg/kg | 6 | 5 | 100% |
| 7 | S2 | 50 mg/kg | 6 | 0 | 0 |
| 8 | S2 | 100 mg/kg | 6 | 0 | 0 |
| 9 | S2 | 150 mg/kg | 6 | 0 | 0 |
| 10 | S2 | 200 mg/kg | 6 | 2 | 33.3% |
| 11 | S2 | 300 mg/kg | 6 | 3 | 50% |
| 17 | doxorubicin hydrochloride | 10 mg/kg | 6 | 6 | 100% |

Results and discussion: no pilo-erection, hair tousle and lackluster, lethargy, stoop, irritable reaction and death were observed in mice receiving 150 mg/kg S1 and S2 injection. As shown in Table 1, the MTD of the S1 and S2 injections were far beyond 100 μmol/kg, and were significantly higher than the MTD of doxorubicin hydrochloride (4-8 μmol/kg). The MTD for intravenous administration of a test drug is an important reference index for drug toxicity. The results indicate that the toxicity of the doxorubicin hydrochloride derivative, which binds to serum albumin, is significantly reduced as compared with doxorubicin hydrochloride.

Test Example 2: Study on Efficacy of S1 and S2 in Nude Mice

Test purpose: to investigate the anti-tumor efficacy of S1 and S2 via mouse tumor treatment model.

Test drug: S1 and S2 injections, and doxorubicin hydrochloride injection, diluted to corresponding concentrations by physiological saline when testing.

Method and Results:

1. Animal: nude mice of 6-8 weeks old, all female.

2. Production of tumor model

1) MDA-MB231 cells were purchased from American type culture collection (ATCC) and identified according the specification provided by ATCC. Cells were cultivated in Dulbecco's minimum essential medium (DMEM culture medium) containing 10% fetal bovine serum at 37° C. and 5% $CO_2$. The cells were passaged for every three days and cells within the 15th passage were used.

2) Production of tumor. $10^6$ MDA-MB231 cells were subcutaneously injected to the back of the nude mice. Mice were randomly grouped after the diameter of the tumor reached about 0.3 cm to 0.4 cm. Then treatment began.

3) Course of treatment

According to the clinical application of S1 and S2, drugs were intraperitoneally injected. A dose of 30 mg/kg (<1/2 MTD) was used for the S1 treatment group, 30 mg/kg (<1/2 MTD) for the S2 treatment group, and 4 mg/kg (>1/2 MTD) for doxorubicin hydrochloride. The control group was administered with physiological saline. The drugs were administered twice weekly for three weeks.

4) Grouping and test results are shown in Table 2.

TABLE 2

Treatment effects of S1, S2, doxorubinin hydrochloride and control on tumors of nude mice

| Group | Number of animal | Size of tumor (mm³) | | Inhibitory rate of tumor | |
|---|---|---|---|---|---|
| | | 20 days | 38 days | 20 days | 38 days |
| S1 group | 10 | 287.42 ± 30.52 | 678.49 ± 37.7 | 25.8% | 68.5% |
| S2 group | 10 | 254.59 ± 34.19 | 618.49 ± 51.27 | 34.3% | 71.3% |
| Control Group (doxorubicin hydrochloride) | 10 | 358.7 ± 39.7 | 881.2 ± 86.5 | 7.4% | 29.1% |
| Model Control | 10 | 387.5 ± 35.6 | 2155.44 ± 325.5 | — | — |

5) Results and discussion: as shown in Table 2, inhibitory effect on tumor in the nude mice after administering with S1 and S2 by intraperitoneal injection was greatly improved as compared with the doxorubicin hydrochloride control group. And S2 could diminish and eliminate the tumor. Results show that this kind of drugs exhibit excellent inhibiting efficacy on tumor growth.

Test Example 3: Study on Efficacy of S1 and S2 in a Tumor Metastasis Model from BALB/C Mice Test purpose: to investigate the anti-tumor efficacy of S1 and S2 in a tumor metastasis treatment model from BALB/C mice.

Test drug: S1 and S2 injections, and doxorubicin hydrochloride injection, diluted to corresponding concentrations with physiological saline when testing.

1. Animal: BALB/C mice of 6-8 weeks old, all female.
2. Production of tumor model 1) 4T1 cells were purchased from American type culture collection (ATCC) and identified according the specification provided by ATCC. Cells were cultivated in DMEM culture medium containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment. According to the clinical application of S1 and S2, drugs were intraperitoneally injected. A dose of 10 µmol/kg (<1/10 MTD) was used for the S1 treatment group, 10 µmol/kg (<1/10 MTD) for the S2 treatment group, and 3 µmol/kg (>1/2 MTD) for doxorubicin hydrochloride. The control group was administered with physiological saline. The drugs were administered daily for 8 days.

4) Grouping and test results are shown in Table 3.

TABLE 3

Effects of S1, S2, doxorubicin hydrochloride and control on inhibition of tumor metastasis in nude mice

| Group | Animal | Number of metastasized tumor | Inhibitory rate on metastasis |
|---|---|---|---|
| S1 group | 10 | 12 ± 4 | 91.6% |
| S2 group | 10 | 10 ± 7 | 93% |
| doxorubicin hydrochloride control group | 10 | 98 ± 18 | 31.4% |
| Model control | 10 | 143.0 ± 29 | — |

Inhibitory rate on metastasis = [1 − (number of metastasized tumors in the treatment group)/(number of metastasized tumors in the control group)] * 100%

5) Results and discussion. As shown in Table 3, the inhibitory effect on tumor metastasis of BALB/C mice was greatly improved after intraperitoneal injection of S1 and S2, as compared with the doxorubicin hydrochloride control group, indicating that this kind of drugs exhibits an excellent efficacy on anti-tumor metastasis.

In some Examples of the present invention (Examples 4-15, synthesized by the same method as in Examples 1-3), toxicity, inhibitory rate on tumor and inhibitory rate on metastasis of some doxorubicin derivatives, which have different substituents and amino acids were tested respectively by the same methods as in the above Test Examples 1-3 and the results are shown in Table 4.

TABLE 4

Activation activity, tumor-inhibitory rate and metastasis-inhibitory rate of Examples 4-15

| Item | $R_1$ | $R_2$ | MDA-MB231 | Tumor-inhibitory rate (day 38) | Metastasis-inhibitory rate |
|---|---|---|---|---|---|
| Example 4 | Ala | Ala | 150 | 55.6% | 84.7% |
| Example 5 | Ala | Thr | 120 | 46.2% | 74.5% |
| Example 6 | Ala | Asn | 130 | 49.5% | 81.6% |
| Example 7 | Thr | Ala | 120 | 51.3% | 77.4% |
| Example 8 | Ala | ALa | 120 | 45.8% | 79.3% |
| Example 9 | Ala | Thr | 120 | 68.3% | 66.8% |
| Example 10 | Ala | Asn | 110 | 58.3% | 84.8% |
| Example 11 | Thr | Ala | 120 | 63.8% | 82.1% |
| Example 12 | Ala | Ala | 140 | 55.2% | 68.3% |
| Example 13 | Ala | Ala | 120 | 47.8% | 71.4% |
| Example 14 | Ala | Ala | 140 | 46.4% | 68.9% |
| Example 15 | Ala | Ala | 140 | 54.6% | 63.5% |
| doxorubicin control group | | | 7 mg/kg | 29.1% | 31.4% |
| Model control | | | — | 0 | 0 |

According to Table 4, the doxorubicin derivatives prepared from condensation of the amino group of the following compound A and the carboxyl of the following compound B could greatly reduce the toxicity of doxorubicin and greatly improve the anti-tumor effect:

Compound A is doxorubicin or its derivative epirubicin;

In compound B, $R_3$ is Leu or absent, $R_4$ is any one amino acid selected from the group consisting of Ala and Thr; $R_5$ is any one amino acid selected from the group consisting of Ala, Thr and Asn; and $R_6$ is

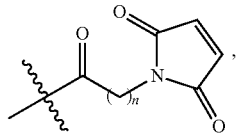

wherein n=1-20; or

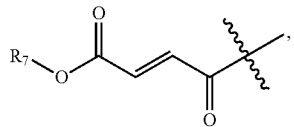

wherein $R_7$ is substituted or unsubstituted, linear or branched, saturated or unsaturated C1-C20 fatty hydrocarbon, or substituted or unsubstituted C6-C20 aromatic hydrocarbon.

The polypeptide doxorubicin of the present invention was functionally modified for tumor targeting by $R_6$, which is preferably EMC or EFA and will be exemplified by EMC below. This modification allows the drug to have the following advantages.

1. Having the Ability of Targeting Tumor

The $R_6$ group allows the drug to be able to target cathepsin (Cathepsin B) in the tumor microenvironment and inhibit the activity of cathepsin necessary for tumor growth, development and metastasis. On the contrary, Succinyl-AANL-DOX (SEQ ID NO: 2) does not exhibit this targeted function. The $R_6$ group also allows the drug to have an additional function of targeting tumor, thus the drug has two targeted effects. In the in vitro binding assay, EMC-AANL-DOX (SEQ ID NO: 2) can efficiently bind to Cathepsin B.

The test method was described as follows. Cathepsin was absorbed on a 96-well plate and blocked with BSA. Succinyl-AANL-DOX (SEQ ID NO: 2), S1 and a mixture of S1 and E-64 (an inhibitor for specific binding of cathepsin) were added to allow them to bind to the cathepsin on the 96-well plate. The unbound drugs were removed and the fluorescence of the bound drug was detected. The results showed that Succinyl-AANL-DOX (SEQ ID NO: 2) did not bind to absorbed cathepsin while S1 bound to the cathepsin. The competitive inhibitory assay indicated that the S1's binding site on the cathepsin was close to the E-64's binding site on the cathepsin, and binding of E-64 could competitively inhibit the binding of S1, as shown in FIG. 1.

Figure 2:
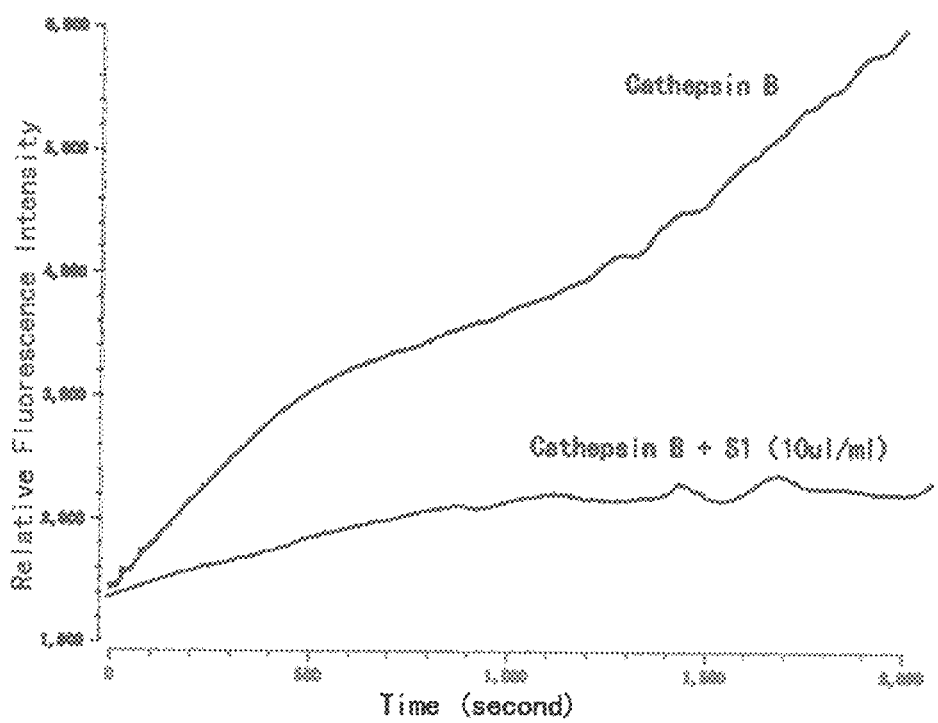
FIG. 2 is a curve showing the experimental results obtained from inhibition of enzymatic activity of cathepsin by S1. The result showing that cross linking between S1 and cysteine of the active center of the enzyme.

Furthermore, Z-Phe-Arg-NMec was used as substrate to analyze the activity of cathepsin under pH 6.0. Results showed that the substrate could be activated by the cathepsin (Cathepsin B) over the time, and the fluorescent intensity was improved. Addition of S1 could effectively inhibit the enzymatic activity of cathepsin, as shown in FIG. 2. Cathepsin B was highly expressed in the lysosome of the tumor cell. It could degrade type I collagen, activate interstitial procollagenase and type IV procollagenase, and degrade type I, II, III and IV collagen fibers in the stroma, thus anticipating infiltration and metastasis of tumor. Inhibiting the enzymatic activity of cathepsin could improve inhibition of infiltration and metastasis of tumor, and inhibiting cathepsin could also inhibit bone metastasis of tumor (such as breast cancer).

2. Improving Retention of Drug at the Tumor Site

Figure 3:
FIG. 3 shows accumulative effects of S1, Dox and Succinyl-AANL-DOX (SEQ ID NO: 2) at the cancer cell. The result showing that the binding between S1 and cathepsin have the effect to accumulate the drug at tumor cell. After cleaving by Legumain, Dox and Leu-DOX become cell penetrating and remain inside cancer cell.
Figure 4:
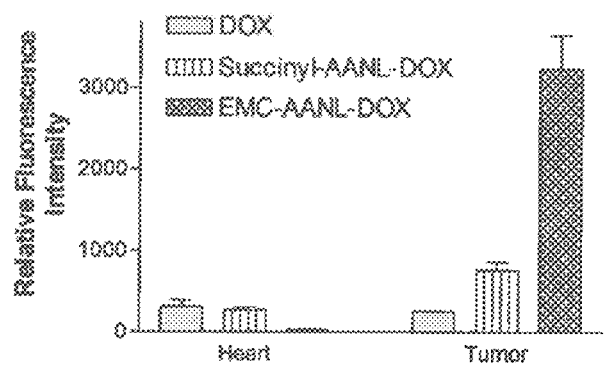
FIG. 4 shows distribution of S1, Dox and Succinyl-AANL-DOX (SEQ ID NO: 2) in the tumor and heart tissues, indicating accumulation of S1 in the tumor site and reduced accumulation in the heart. The result showing that the binding and activation cause drug selectively accumulate in tumor tissue. With a low concentration in normal tissue, the S1 have no toxicity to heart.

After intravenous injection of EMC-AANL-DOX (SEQ ID NO: 2), EMC-AANL-DOX (SEQ ID NO: 2) could accumulate at the tumor site due to the targeting property of the EMC group, as compared with Succinyl-AANL-DOX (SEQ ID NO: 2) and more EMC-AANL-DOX (SEQ ID NO: 2) were distributed in the tumor tissue. Since the drug itself could produce fluorescence, we detected distribution of Succinyl-AANL-DOX (SEQ ID NO: 2) and EMC-AANL-DOX (SEQ ID NO: 2) in the tumor tissue sections by fluorescence microscope 12 hours after intravenous injection of 10 μmol/kg Succinyl-AANL-DOX (SEQ ID NO: 2) and EMC-AANL-DOX (SEQ ID NO: 2). The nucleus was stained by 4',6-diamidino-2-phenylindole (DAPI). As shown in FIG. 3, significantly more EMC-AANL-DOX (SEQ ID NO: 2) were distributed in the tumor tissue, indicating that EMC-AANL-DOX (SEQ ID NO: 2) improved retention of drug in the tumor site. FIG. 4 shows the distribution of D1, Dox and Succinyl-AANL-DOX (SEQ ID NO: 2) in the tumor and heart tissues. As shown in FIG. 4, EMC-AANL-DOX (SEQ ID NO: 2) accumulated in a higher concentration in the tumor tissue as compared with doxorubicin and Succinyl-AANL-DOX (SEQ ID NO: 2), with no accumulation in the heart tissue. These results demonstrated that EMC-AANL-DOX (SEQ ID NO: 2) could improve the targeting to the tumor and avoid heart toxicity caused by accumulation of Dox in the heart.

3. Improving the Efficacy

The efficacy of Succinyl-AANL-DOX (SEQ ID NO: 2) and EMC-AANL-DOX (SEQ ID NO: 2) in BALB/C mice were studied and compared.

Test purpose: to investigate the anti-tumor efficacy of Succinyl-AANL-DOX (SEQ ID NO: 2) and EMC-AANL-DOX (SEQ ID NO: 2) in a 4T1 breast cancer treatment model from BALB/C mice.

Treatment drug: Succinyl-AANL-DOX (SEQ ID NO: 2) and EMC-AANL-DOX (SEQ ID NO: 2) injections, and doxorubicin hydrochloride injection, diluted to corresponding concentrations by physiological saline when testing.

1. Animal: BALB/C mice of 6-8 weeks old, all female.
2. Production of tumor model 1) 4T1 cells were purchased from American type culture collection (ATCC) and identified according the specification provided by ATCC. Cells were cultivated in Dulbecco's modified eagle medium (DMEM) containing 10% fetal bovine serum at 37° C. and 5% $CO_2$. The cells were passaged for every three days and cells within the 15th passage were used.

2) Production of tumor. $10^6$ 4T1 cells were subcutaneously injected to the back of the BALB/C mice. Mice were randomly grouped after the diameter of the tumor reached about 0.3 cm to 0.4 cm. Then treatment began.

3) Course of treatment

Succinyl-AANL-DOX (SEQ ID NO: 2), Legubicin and EMC-AANL-DOX (SEQ ID NO: 2) were intraperitoneally injected. The dose of Succinyl-AANL-DOX (SEQ ID NO: 2), Legubicin and EMC-AANL-DOX (SEQ ID NO: 2) were all 28.16 μmol/kg. The dose of doxorubicin hydrochloride was 3.448 μmol/kg. The control group was administered with physiological saline. The drugs were administered twice weekly for three weeks.

Figure 5:
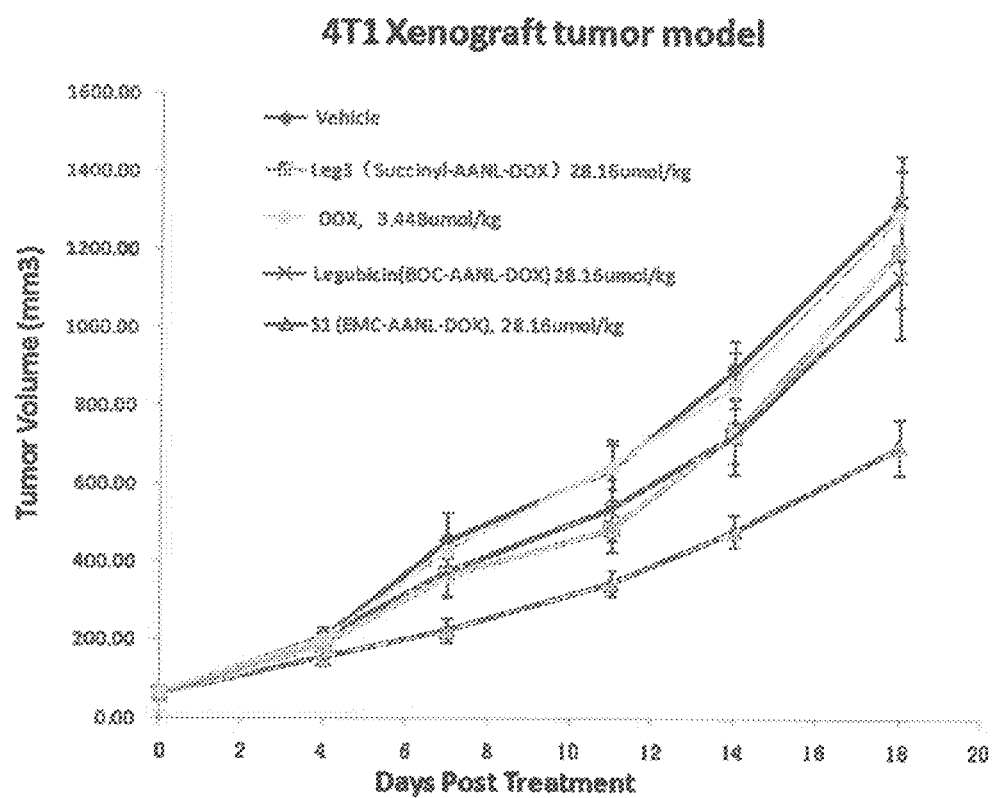
FIG. 5 is a curve showing the tumor-inhibiting effects of S1 of the present invention, Dox, Succinyl-AANL-DOX (SEQ ID NO: 2), Legubicin and solvent control (Vehicle) on the 4T1 breast cancer model, indicating that EMC-AANL-DOX (SEQ ID NO: 2) exhibits a superior inhibitory effect on tumor growth over Dox, BOC-AANL-DOX (SEQ ID NO: 2) and Succinyl-AANL-DOX (SEQ ID NO: 2).

4) Results and discussion. FIG. 5 showed the curve indicating inhibitory effect on tumor growth in the 4T1 breast cancer model by S1, Dox, Succinyl-AANL-DOX (SEQ ID NO: 2), Legubicin and solvent control (Vehicle). As shown in FIG. 5, EMC-AANL-DOX (SEQ ID NO: 2) could significantly improve the inhibitory effect on tumor growth in the BALB/C mice after intraperitoneal inject, as compared with Succinyl-AANL-DOX (SEQ ID NO: 2), Dox, and BOC-AANL-DOX (SEQ ID NO: 2).

Figure 6:
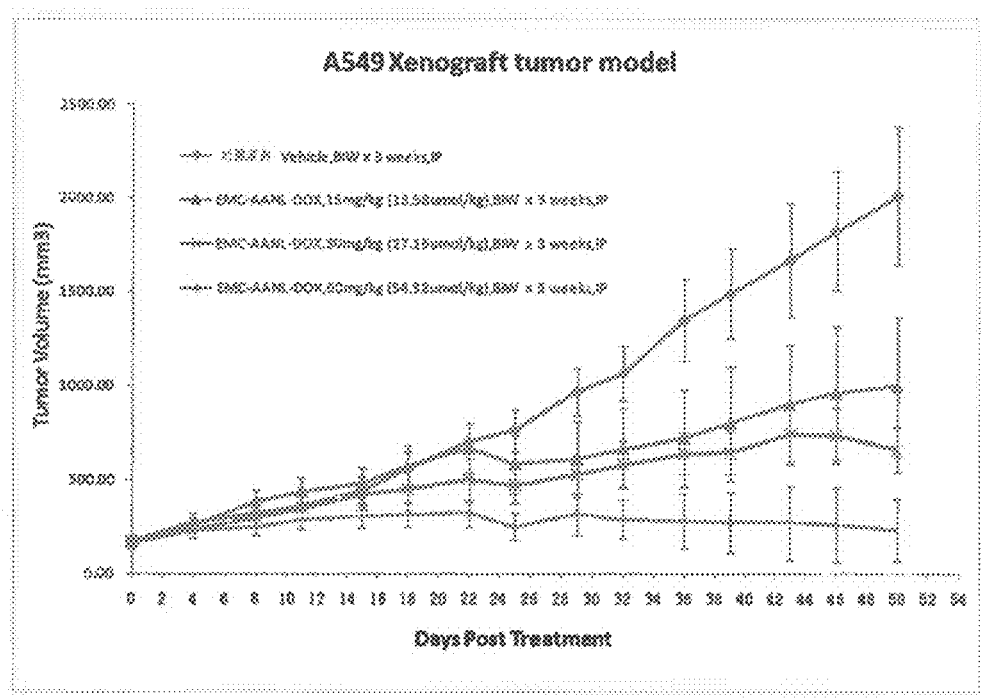
FIG. 6 is a curve showing the tumor-inhibiting effects of S1 of the present invention, used in different doses, on a human non-small cell lung cancer model (A549), indicating that the efficacy of EMC-AANL-DOX (SEQ ID NO: 2) satisfies our requirements on further clinical development.

In some examples and many other tumor treatment modes of the present invention, efficacies of Succinyl-AANL-DOX (SEQ ID NO: 2) and EMC-AANL-DOX (SEQ ID NO: 2) were also studied and compared according to the same method as described above. It was found that the inhibitory effect of EMC-AANL-DOX (SEQ ID NO: 2) on tumor growth was greatly improved in the 4T1 breast cancer model, etc., which was about 4-5 folds of Succinyl-AANL-DOX (SEQ ID NO: 2). And, in efficacy assays using different doses, it was found that only EMC-AANL-DOX (SEQ ID NO: 2) could completely kill the tumor, with no recurrence of tumor in the later stage of the treatment, as shown by the human non-small cell lung cancer A549 model in FIG. 6. Thus, EMC-AANL-DOX (SEQ ID NO: 2) could satisfy our requirements on clinical development.

4. Changing in drug metabolism and greatly improving metabolic half-life of the drug The $R_6$ group changed the metabolic state of the drug, such as S1. After intravenous injection, Succinyl-AANL-DOX (SEQ ID NO: 2) did not bind to serum albumin in the blood plasma and was metabolized in the blood as free small molecule. However, after entering into blood, S1 could bind to the serum albumin. S1 and Succinyl-AANL-DOX (SEQ ID NO: 2) were intravenously injected at the tail. Bloods were taken after 10 minutes and centrifuged to obtain serum. The proteins in the serum were precipitated by 70% ethanol. The results showed that after entering into the blood, most of S1 could bind to serum albumin and thus precipitated. On the contrary, Succinyl-AANL-DOX (SEQ ID NO: 2) was still present in the supernate. These results demonstrated that doxorubicin drug, such as S1, modified by $R_6$, was a drug having a completely different metabolism.

In some examples of the present invention, it was also found that, after entering into the blood, most of S1 bound to the plasma protein and the metabolic half-life of S1 in the mice blood was increased to above 74 hours, as compared with 42 minutes for BOC-AANL-DOX (SEQ ID NO: 2) and 37 hours for Succinyl-AANL-DOX (SEQ ID NO: 2).

In summary, the present invention synthesizes derivatives of doxorubicin hydrochloride, which could be activated by Legumain and target to cathepsin and were demonstrated by toxicity and efficacy assays to provide lower toxicity, more significant anti-tumor activity and inhibition of tumor metastasis than doxorubicin hydrochloride and Succinyl-AANL-DOX (SEQ ID NO: 2).

Although the contents of the present invention were illustrated in detail via the above preferred embodiments, it should be understood that the above descriptions shall not be construed as limitation on the present invention. Many modifications and replacements are apparent to the skilled artisan after reading the above contents. Therefore, the protection scope of the present invention should be defined by the attached claims.

The invention claimed is:

1. A doxorubicin derivative for targeted activation by Legumain, having the following structural formula:

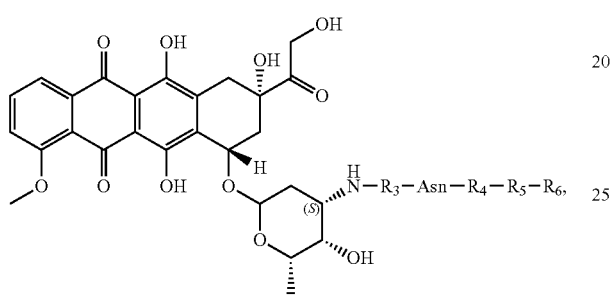

wherein the doxorubicin derivative is prepared by condensation between the amino group of compound A and the carboxyl group of compound B, and compounds A and B have the following structures, respectively:

Compound A

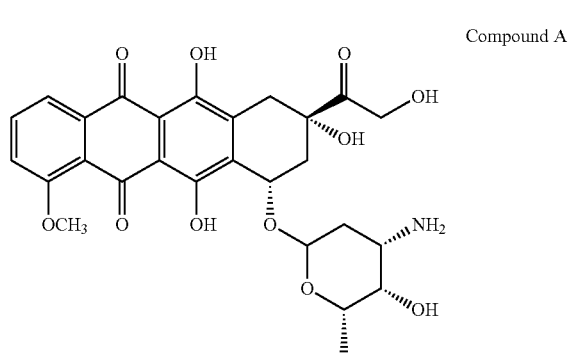

Compound B $R_3$—Asn—$R_4$—$R_5$—$R_6$ wherein compound A is doxorubicin or its derivative;

wherein $R_3$ in compound B is Len or absent; if $R_3$ is absent then compound B is a tripeptide, that is, the carboxyl of Asn covalently condensates with the amino of compound A directly to produce a polypeptide doxorubicin; if $R_3$ is Len, then compound B is a tetrapeptide, that is Leu-Asn-$R_4$-$R_5$—;

$R_4$ is any one amino acid selected from the group consisting of Ala and Thr;

$R_5$ is any one amino acid selected from the group consisting of Ala, Thr and Asn;

$R_6$ is

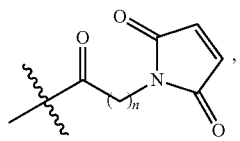

wherein n=1-20; or

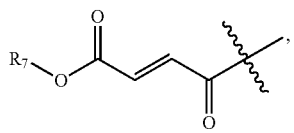

wherein $R_7$ is substituted or unsubstituted, linear or branched, saturated or unsaturated C1-C20 fatty hydrocarbon, or substituted or unsubstituted C6-C20 aromatic hydrocarbon.

2. The doxorubicin derivative for targeted activation by Legumain of claim 1, wherein compound A is doxorubicin or epirubicin, and epirubicin is an isomer of doxorubicin and has the following structure:

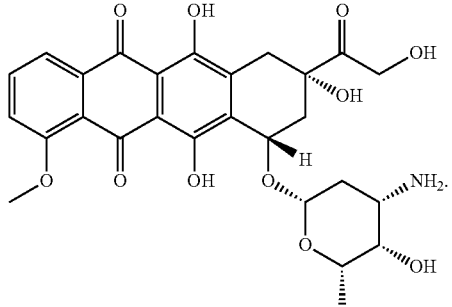

3. The doxorubicin derivative for targeted activation by Legumain of claim 1, wherein $R_6$ is

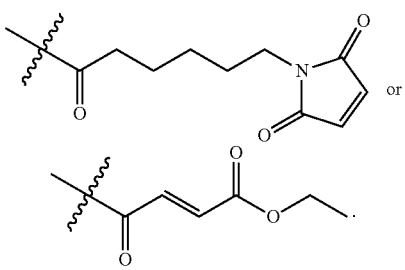

4. The doxorubicin derivative for targeted activation by Legumain of claim 3, wherein the doxorubicin derivative is S1 having the following structure:

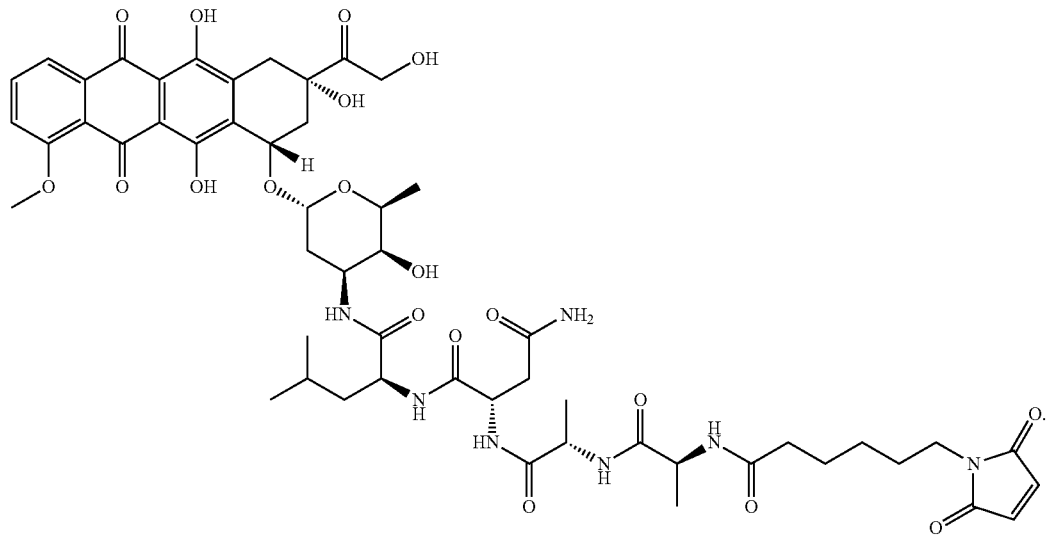 [SMILES: COc1cccc2c1C(=O)c1c(O)c3c(c(O)c1C2=O)C[C@@](O)(C(=O)CO)C[C@@H]3O[C@H]1C[C@H](NC(=O)[C@H](CC(C)C)NC(=O)[C@H](CC(N)=O)NC(=O)[C@H](C)NC(=O)[C@H](C)NC(=O)CCCCCN2C(=O)C=CC2=O)[C@H](O)[C@H](C)O1]

5. The doxorubicin derivative for targeted activation by Legumain of claim 3, wherein the doxorubicin derivative is S2 having the following structure:

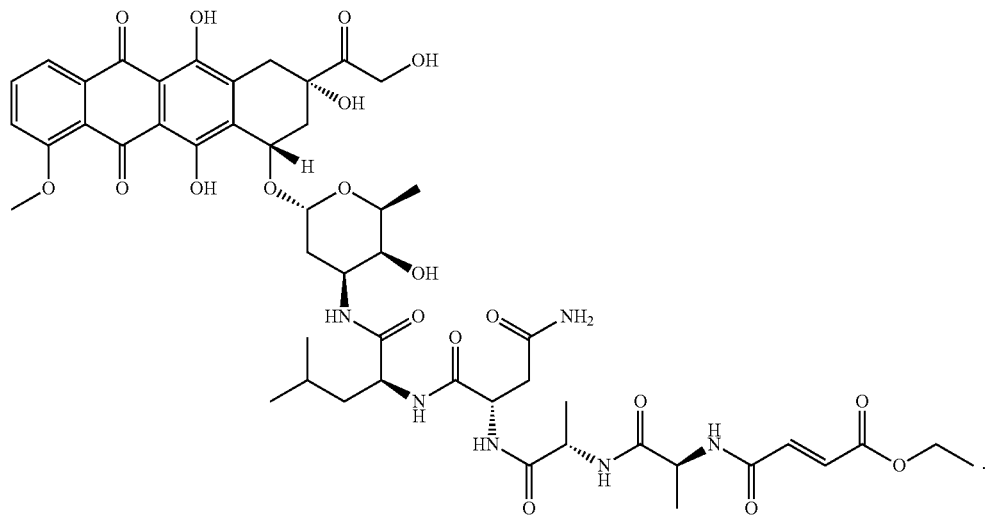 [SMILES: CCOC(=O)/C=C/C(=O)N[C@@H](C)C(=O)N[C@@H](C)C(=O)N[C@@H](CC(N)=O)C(=O)N[C@@H](CC(C)C)C(=O)N[C@H]1C[C@H](O[C@H]2C[C@](O)(C(=O)CO)Cc3c(O)c4c(c(O)c32)C(=O)c2c(OC)cccc2C4=O)O[C@@H](C)[C@H]1O]

6. A method for preparing the doxorubicin derivative for targeted activation by Legumain of claim 1, comprising the following steps:

Step 1, preparing a tripeptide or a tetrapeptide, $R_3$-Asn-$R_4$-$R_5$, by conjugating the amino acid residues together and isolating to obtain the formed tripeptide or tetrapeptide $R_3$-Asn-$R_4$-$R_5$, Step 2, preparing compound B by reacting $R_3$-Asn-$R_4$-$R_5$ obtained in step 1 with the acyl or carboxyl of $R_6$—Cl or $R_6$—OH to obtain $R_3$-Asn-$R_4$-$R_5$-$R_6$;

Step 3, covalently condensating the carboxyl group in $R_3$ of the compound $R_3$-Asn-$R_4$-$R_5$-$R_6$ obtained in step 2 with the amino group of compound A to form the doxorubicin derivative for targeted activation by Legumain.

7. The method for preparing the doxorubicin derivative for targeted activation by Legumain according to claim 6, wherein $R_3$ in compound B is Len or absent; $R_4$ is any one amino acid selected from the group consisting of Ala and Thr; $R_5$ is any one amino acid selected from the group consisting of Ala, Thr and Asn; and $R_6$ is

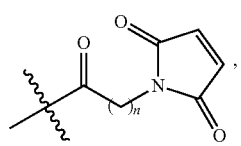

wherein n=1-20; or

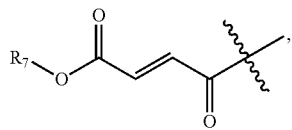

wherein $R_7$ is substituted or unsubstituted, linear or branched, saturated or unsaturated C1-C20 fatty hydrocarbon, or substituted or unsubstituted C6-C20 aromatic hydrocarbon.

8. The method for preparing the doxorubicin derivative for targeted activation by Legumain according to claim 6, wherein $R_6$ is:

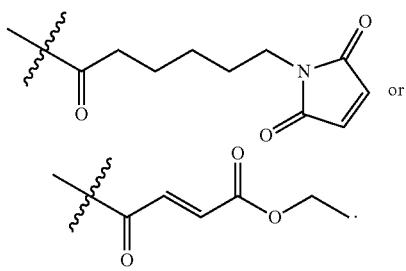

9. The doxorubicin derivative for targeted activation by Legumain according to claim 1 in the preparation of an anti-tumor drug.

10. The doxorubicin derivative for targeted activation by Legumain according to claim 1, wherein the cleavable linker is Legumain comprising a peptide sequence selected from Leu-Asn-Ala-Ala, Leu-Asn-Ala-Thr, Leu-Asn-Ala-Asn, Leu-Asn-Thr-Ala, Leu-Asn-Thr-Thr, Leu-Asn-Thr-Asn.

11. The doxorubicin derivative for targeted activation by Legumain according to claim 1, where in the cleavable linker is Legumain and further wherein cleaving occurs at the peptide bond between Leu and Asn thereby releasing Leu-doxorubicin and Leu-epirubicin.

12. A medicament comprising at least one compound of claim 5 for the treatment of cancer or related neoplastic disease.

13. A method for treating cancer in a mammal comprising administering a therapeutically effective amount of the compound of claim 1 to a mammal in need thereof.

14. The method of claim 13, wherein the cancer is selected from the group consisting of non-small cell lung cancer (NSCLC), liver, colon, kidney, thyroid, pancreatic, head and neck, prostate, ovarian, breast and sarcoma.

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn(Trt)

<400> SEQUENCE: 1

Ala Ala Asn Leu
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Asn Leu
1

<210> SEQ ID NO 3
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Leu Asn Ala Ala
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Asn Ala Thr
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Asn Ala Asn
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Asn Thr Ala
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Asn Thr Thr
1

<210> SEQ ID NO 8
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 8

Leu Asn Thr Asn
 1
```